(12) United States Patent
Yang et al.

(10) Patent No.: US 8,475,811 B2
(45) Date of Patent: Jul. 2, 2013

(54) PREMIXED BIOLOGICAL HYDRAULIC CEMENT PASTE COMPOSITION AND USING THE SAME

(75) Inventors: Quanzu Yang, Vancouver (CA); Donghui Lu, Vancouver (CA)

(73) Assignee: Innovative BioCeramix, Inc., Vancouver, B.C. (CA)

( * ) Notice: Subject to any disclaimer, the term of this patent is extended or adjusted under 35 U.S.C. 154(b) by 1219 days.

(21) Appl. No.: 12/148,741

(22) Filed: Apr. 21, 2008

(65) Prior Publication Data

US 2008/0299093 A1    Dec. 4, 2008

Related U.S. Application Data

(60) Provisional application No. 60/925,183, filed on Apr. 20, 2007.

(51) Int. Cl.
*A61K 33/00* (2006.01)
*A61K 9/00* (2006.01)

(52) U.S. Cl.
USPC .......................................... 424/400; 424/600

(58) Field of Classification Search
USPC ................................. 424/400, 600
See application file for complete search history.

(56) References Cited

U.S. PATENT DOCUMENTS

| | | | |
|---|---|---|---|
| 4,433,958 A * | 2/1984 | Fellman et al. ............ | 433/199.1 |
| 5,415,547 A | 5/1995 | Torabinejad et al. | |
| 5,769,638 A | 6/1998 | Torabinejad et al. | |
| 6,284,030 B1 * | 9/2001 | Orlowski et al. ............... | 106/35 |
| 2003/0159618 A1 | 8/2003 | Primus | |

FOREIGN PATENT DOCUMENTS

| | | |
|---|---|---|
| WO | WO02/062721 | 8/2002 |
| WO | WO2004/093734 | 11/2004 |
| WO | WO2006/099748 | 9/2006 |
| WO | WO2007/047994 | 4/2007 |
| WO | WO 2007/051290 | 5/2007 |

OTHER PUBLICATIONS

Gou, et al., "Synthesis and in vitro bioactivity of dicalcium silicate powders" Journal of the European Ceramic Society 24 (2004) 93-99.

Ni, et al. (Journal Biomedical Material Res Part B: Appl Biomater 80B: 174-183, 2007).

Vargas, et al., "A Comparison of the in vitro Retentive Strength of Glass-Ionomer Cement, Zinc-Phosphate Cement, and Mineral Trioxide . . . " J. Endodont. 30(11)(2004), 775-777.

Torabinejad, et al., "Physical and Chemical Properties of a New Root-End Filling Material" J. Endodont. 21 (1995) 349-253.

Lee, et al., "Sealing Ability of a Mineral Trioxide Aggregate for Repair of Lateral Root Perforations" J. Endodont. 1993; 19:541-4.

Mitchell, et al., "Osteoblast Biocompatibility of Mineral Trioxide Aggregate" Biomaterials 20 (1999) 167-173.

Takagi, et al., (Journal Biomedical Material Res Part B: Appl Biomater 67B: 689-696, 2003).

Xu, et al., "Premixed Calcium Phosphate Cements: Synthesis, Physical Properties, and Cell Cytotoxicity" dental materials 23 (2007) 433-441.

\* cited by examiner

*Primary Examiner* — Ruth Davis
(74) *Attorney, Agent, or Firm* — Todd N. Hathaway

(57) ABSTRACT

A premixed cement paste for use in medical or dental applications. The premixed cement paste remains fluid when stored in a hermetically sealed condition, but hydrates and hardens to set when placed in a physiological environment. The cement paste includes at least one calcium silicate compound and at least one substantially water-free liquid carrier mixed with the at least one calcium silicate compound; the substantially water-free liquid carrier avoids hydration of the mixture during storage, but undergoes exchange with aqueous physiological solutions so that the cement past hydrates and hardens to set when placed in a physiological environment. The paste may be placed in the physiological environment by injection, for example. The at least one calcium silicate compound may be, for example, calcium silicate, dicalcium silicate, tricalcium silicate, or mixtures thereof. The substantially water-free liquid may be, for example, ethylene glycol, polyethylene glycol, liquid glycerol, glycerin, ethyl alcohol, vegetable oil, animal oil, silicon oil, hydroxypropyl methylcellulose, or mixtures thereof. The substantially water-free liquid carrier preferably includes water in an amount less than about 20% by weight percent of the paste. The paste may include a secondary phase for enhanced properties, such as, for example, a fibrous or particulate material for enhanced mechanical properties, biodegradable or soluble materials that provide room for bone in-growth, bioactive materials such as antibiotics that elute into the physiological environment from the set cement, and radio-opaque materials that enhance X-ray imaging of the cement.

14 Claims, 5 Drawing Sheets

PREMIXED BIOLOGICAL HYDRAULIC CEMENT PASTE COMPOSITION AND USING THE SAME

RELATED APPLICATIONS

This application claims the benefit of U.S. Provisional Patent Application Ser. No. 60/925,183 filed on Apr. 20, 2007.

FIELD OF THE INVENTION

The present invention relates to hydraulic cements for biomedical applications, and, more particularly, to a premixed paste composition of biological hydraulic cement for dental and orthopedic applications.

BACKGROUND OF THE INVENTION

Calcium silicates (monocalcium silicate CS, di-calcium silicate C2S and tri-calcium silicate C3S) are well known to hydrate and set and harden when mixed with water, through precipitation of gel-like calcium silicate hydrate (Ca—Si—$H_2O$ gel) (C—S—H), similar to ordinary Portland cement (OPC).

The open literature indicates that hydroxyapatite nuclei can form and grow on hydrated calcium silicate particles, and therefore hydrated calcium silicates are potential candidates as biomaterials for hard tissue repair (Gou, et al., "*Synthesis and in vitro bioactivity of dicalcium silicate powders*" *Journal of the European Ceramic Society* 24 (2004) 93-99). Also, Ni et al (*J Biomed Mater Res Part B: Appl Biomater* 80B: 174-183, 2007) investigated "Comparison of Osteoblast-Like Cell Responses to Calcium Silicate and Tricalcium Phosphate Ceramics In Vitro". The results indicate that calcium silicate ceramics are biocompatible and bioactive and therefore suitable as new bone repair biomaterials.

Recently, certain Portland cement—based materials (referred to as mineral trioxide aggregate, MTA) have been also used for dental applications, such as endodontic dental treatment and the retention of a core (Vargas et al., "*A Comparison of the In vitro Retentive Strength of Glass-Ionomer Cement, Zinc-Phosphate Cement, and Mineral Trioxide Aggregate for the Retention of Prefabricated Posts in Bovine Incisors*" *J. Endodont.* 30(11) 2004, 775-777). MTA is a Portland cement-like material, which consists primarily of tricalcium silicate, tricalcium oxide, and tricalcium aluminates [Torabinejad et al. "*Physical and chemical properties of a new root-end filling material*". *J Endodont* 21(1995) 349-253]. MTA has been used in many surgical and non-surgical applications, and possesses the biocompatibility and sealing abilities requisite for a perforation material (Lee, et al, "*Sealing ability of a mineral trioxide aggregate for repair of lateral root perforations*" *J Endod* 1993;19:541-4.). It can be used both as a non-absorbable barrier and restorative material for repairing root perforations. Because it is hydrophilic and requires moisture to set, MTA is the barrier of choice when there is potential for moisture contamination or when there are restrictions in technical access and visibility.

The physical and chemical properties of MTA have been tested and the initial pH on mixing was 10.2 rising to 12.5 after 3 h; it also has good compressive strength after setting. The MTA was demonstrated to be significantly less toxic than other root-end filing materials when freshly mixed, and toxicity was negligible when fully set at 24 h (Mitchell, et al, "*Osteoblast biocompatibility of mineral trioxide aggregate*" *Biomaterials* 20 (1999) 167-173)

Torabinejad et al (U.S. Pat. No. 5,415,547, U.S. Pat. No. 5,769,638) disclosed an improved method for filing and sealing tooth cavities, which involves the use of an MTA cement composition, including the ability to set in an aqueous environment. The cement composition comprises Portland cement, or variations in the composition of such cement, which exhibit favorable physical attributes sufficient to form an effective seal against re-entrance of infectious organisms. However, the cement is gray in color, which is unsuitable for many dental applications.

Primus (US Patent Appl. No. 2003/0159618) disclosed a process for making a white, substantially non-iron containing dental material based on a Portland cement composition. The material may be used as a dental cement, dental restorative or the like. However, this process only decreased the iron content but did not improve biological properties of these materials.

LU et al (PCT/CA2006/001761) disclosed a composition of hydraulic cement for medical applications comprising calcium silicates and phosphates, referred to as Calcium Phosphate Silicate Cement (CPSC), which employs in-situ setting and hardening. The composition is claimed to be suitable for dental, implants, bone fixation, and bone repair applications. The CPSC has high mechanical strength, adjustable setting time, low hydration heat, resistance to bio-degradation, high bioactivity and biocompatibility, and stability against corrosive environments. The cement employs a novel chemical process of in-situ formation of hydroxyapatite/calcium silicate hydrate gel composite at room- or nearly room-temperature and pressure, accompanied by the removal of calcium hydroxide $Ca(OH)_2$, referred to as CH, during cement hydration. This is accomplished through in-situ reacting the CH with phosphate ions to precipitate much stronger and chemically resistant calcium phosphate, in particular hydroxyapatite (HAP), intimately mixed with the C—S—H gel resulting from hydration of calcium silicates. As a result of this in-situ chemical precipitation process the composite cement has high mechanical strength, but also biocompatibility, bioactivity, and adjustable setting time. These properties do not require application of hydrothermal treatment or pressure-assisted forming of the components. However, like the MTA and Calcium Phosphate Cement (CPC) described above, the CPSC powder must be mixed with water to initiate the hydration and setting process.

Mixing and handling of cements is a key aspect of any particular application. For clinical uses, it is very important to properly mix the cement with liquid, such as water, and then place the cement paste in the defect within the prescribed time, which is a crucial factor in achieving optimum results. One of the main issues related to the mixing process is insufficient and inhomogeneous mixing of solids with liquids, or improper ratio of cement solids to water, thus compromising the implant placement, setting process, set properties, and thus performance. It is therefore desirable that cements be premixed under well-controlled conditions; premixing is widely practiced in construction, e.g., premixed concrete delivered in trucks, however, hydraulic cements premixed with water have rather short working time and must be delivered to the application site immediately. Another issue, specific to medical cements, is that all the individual components of the cement material and the equipment need to be sterilized, and the mixing needs to be performed in a sterile environment. Also, mixing time may understandably increase the total surgical placement time. Thus, it would be desirable to have a premixed cement paste that is stable in the sterile package for extended period of time, that is easy to implant after the package is opened, and that hardens only after being placed in the defect.

Takagi, et al (*J Biomed Mater Res Part B: Appl Biomater* 67B: 689-696, 2003) reported the results of research involving Premixed Calcium Phosphate Cement (CPC) pastes. The premixed pastes were prepared by mixing water-free glycerol and calcium phosphate cement powder to form a stable paste. The calcium phosphate cement hardened only after being delivered to a defect site where glycerol-tissue fluids exchange occurred. However, set calcium phosphate cement is biodegradable and has relatively low mechanical strength, and therefore is not suitable for many medical or dental applications. (Xu, et al, "*Premixed calcium phosphate cements: Synthesis, physical properties, and cell cytotoxicity*" dental materials 23 (2007) 433-441).

SUMMARY OF THE INVENTION

The present invention has solved the problems cited above and is a premixed calcium silicate cement paste for dental, orthopedic and other biomedical applications. The premixed biocement paste (PBP) hydrates and sets to non-biodegradable, high-strength C—S—H gel upon exchange of the paste liquid into water-based body fluids.

The novel Premixed Biocement Paste (PBP) comprises at least one type of calcium silicate and at least one substantially water-free liquid. The PBP paste is prepared by mixing the substantially water-free liquid and the calcium silicates. The paste does not set and harden in sealed package because calcium silicate cements hydrate and harden only when exposed to an aqueous environment. After the PBP paste is placed in contact with a physiological solution, exchange of the non-aqueous liquid carrier by the aqueous physiological solution leads to cement hydration and hardening. These reactions involve hydration of calcium silicate compounds, such as C2S or C3S, to produce calcium silicate hydrate gel C—S—H and calcium hydroxide.

The calcium silicates are the main components the cement and provide it with biocompatible and bioactive properties. The monocalcium silicate ($CaSiO_3$), dicalcium silicate ($Ca_2SiO_4$) and tricalcium silicate ($Ca_3SiO_5$) powders were synthesized by sol-gel process and hydrothermal synthesis. The in vitro bioactivity of $Ca_2SiO_4$ and $Ca_3SiO_5$ has been demonstrated by soaking the hydrated powders in simulated body fluid (SBF) for various time periods to analyze the nucleation and growth of hydroxyapatite (HAp) on the surface of the powders.

In dental and certain orthopedic applications, radio-opaque materials may be included in the composition of the PBP paste for improving absorption of X-rays and therefore enhanced X-ray imaging. Radio-opacity materials include, but are not limited to, Barium sulfate, Zirconium oxide, Bismuth oxide, tantalum oxide, and a mixtures thereof. Radio-opacity is important for uses of cements in dental filling and dental sealing. For some dental applications, however, it is not necessary to have high radio-opacity, for instance, pulp capping and decay repair.

The premixed paste may include secondary additives suitable for any particular biological application, including chemical (reactive) modifiers such as phosphates, or non-reactive modifiers such as fillers and fibers for modifying the microstructure and mechanical properties of set cement. For example, bioactive agents may be incorporated into the PBP for controlled release. Bioactive agents include, but not limited to, anti-inflammatory drugs, antibiotics, anti-cancer drugs, proteins, and DNA. Various forms of filler materials (particles or fibers; reactive or non-reactive) may also be incorporated into the composition of novel paste PBP for improvement mechanical and biological properties, such as polymer materials, powders, and metals. In particular, inclusion of phosphates in the premixed cement paste will cause the paste to hydrate and set to non-biodegradable high strength C—S—H gel/HAP nanocomposite upon exchange of the paste liquid into water-based body fluids.

These and other features and advantages of the present invention will be more fully understood and appreciated from a reading of the following detailed description with reference to the accompanying drawings.

BRIEF DESCRIPTIONS OF THE DRAWINGS

FIG. 1 is a Scanning Electron Microscope (SEM) image illustrating the results of a bioactivity test for one variant of the PBP calcium silicate paste of the present invention, with approximately 10% of the calcium phosphates co-precipitated with C—S—H gel, the samples having been immersed in SBF (Simulated Body Fluid) solution at 37° C. for 10 days, showing a typical hydroxyapatite structure layer having been formed on the surface of the cement and thereby demonstrating that the PBP cement possesses high bioactivity;

DETAILED DESCRIPTION

Figure 1:
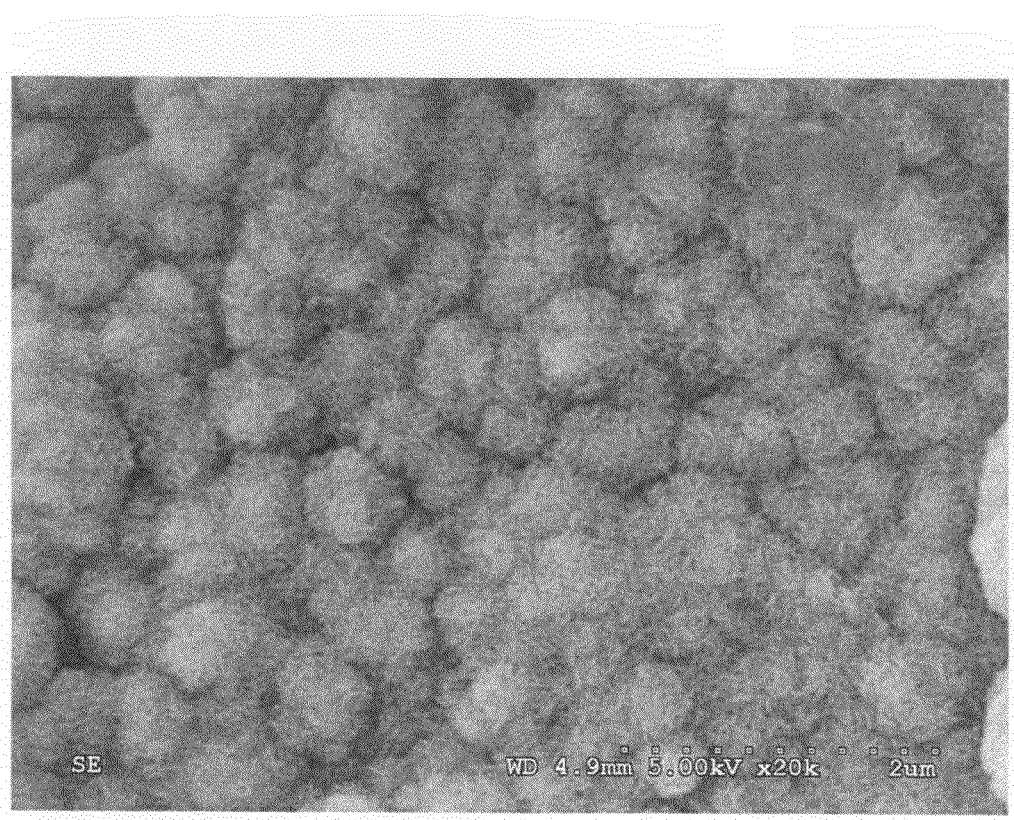

The present invention discloses a novel premixed paste of biological hydraulic cement for biomedical applications, in particular dental and orthopedic applications. The paste is referred to herein as Premixed BioCement Paste, or PBP in short. The PBP comprises at least one type of calcium silicate and at least one substantially water-free liquid. PBP has high mechanical strength after setting, adjustable setting time, low hydration heat, good resistance to degradation, high bioactivity and biocompatibility, and stability in corrosive environments. The PBP is made by mixing a substantially water-free liquids or liquids and calcium silicate or silicates.

As used herein with respect to the liquid carrier, the term "substantially water-free" means waterless or containing water in a an amount sufficiently small that the paste will not undergo hydration and setting when kept in a hermitically-sealed condition; for the use with the preferred composition described herein, water will preferably be present in the carrier in an amount no greater than about 20 percent by weight percent of the paste.

Other additives (reactive and non-reactive, or medically active such as drugs, proteins or DNA) may be included in the base PBP composition, as desired for or required by any particular biomedical application. The resulting injectable cement paste PBP does not set and harden in the sealed package, because calcium silicate cements hydrate only when exposed to aqueous environment. After the PBP paste is placed in contact with a physiological solution, exchange of the non-aqueous carrier by the aqueous solution leads to the PBP setting and hardening. These reactions involve hydration of calcium silicate compounds to produce calcium silicate hydro-gel and calcium hydroxide.

As noted above, the major components of the PBP comprise at least one calcium silicate compound and at least one substantially water-free liquid compound. Examples of calcium silicate compounds that can be used include, but are not limited to, monocalcium silicate CS ($CaO.SiO_2$), dicalcium silicate C2S ($2CaO.SiO_2$), tricalcium silicate C3S ($3CaO.SiO_2$), and mixtures thereof. Examples of suitable substantially water-free liquid include, but are not limited to, ethyl alcohol, ethylene glycol, polyethylene glycol (PEG), glycerol liquid, glycerin, liquid organic acids, vegetable oil, animal oil, fish oil, and mixtures thereof. The water content in the substantially water-free liquid is preferably less than 20 wt %.

The calcium silicates may be included in the range of about 20%-90% by weight in the paste composition, preferably in the range of 30 wt %-70 wt %. The total solid components in the PBP may be in the range of about 30%-95% by weight in the paste composition, preferably in the range of about 60 wt %-90 wt %. The liquid components of PBP may be in the range of about 5%-70% by weight in the paste composition, preferably in the range of about 10 wt %-40 wt %.

Other calcium compounds that may be included in the PBP paste composition, include, but are not limited to, calcium oxide, calcium carbonates, calcium hydroxides, calcium sulfates, calcium phosphate, and mixtures thereof. Phosphate compounds may be introduced into the PBP paste composition, including but not limited to, calcium phosphates, magnesium phosphates, sodium phosphates, zinc phosphates, iron phosphates, potassium phosphates, nickel phosphates, zirconium phosphates, phosphoric acid, organo-metallic phosphates, and a mixtures thereof. The phosphates used in the PBP may contain hydration water. More complex (pre-reacted) phosphates may also be used. Calcium phosphates that may be used in the PBP include, but are not limited to, calcium phosphate monobasic, dicalcium phosphate, tri-calcium phosphate, tetra-calcium phosphates, and mixtures thereof. The calcium phosphates may contain hydration water.

In another embodiment of the present invention, a second phase was incorporated into the PBP for improving the physical, mechanical, chemical, and biological of properties of the set PBP cement paste. In general, ceramic matrix composites (CMCs) combine reinforcing ceramic phases with ceramic matrixes to create materials with new and superior properties that overcome the disadvantages of brittle ceramics. If brittle (catastrophic) fracture is replaced by stable fibrous fracture, ceramic composites may be used reliably as engineering materials for structural and other high performance applications. The failure of fiber-reinforced composite is to a large extent determined by the nature of the interface between the reinforcement fiber and the surrounding matrix. The high toughness results when energy is absorbed as fibers pull out from the matrix as the composite cracks. Thus, a low interfacial stress or friction is needed to ensure fibrous fracture. If a strong interfacial bond exists, the crack will cut through the fiber without pulling out the fiber, resulting in a fracture behavior not much different from unreinforced monolithic ceramics. For hydraulic calcium silicate based cements, as for any brittle ceramic material, tensile strength is significantly lower (by a factor of ~10) as compared to compressive strength, which is fundamentally related to low fracture toughness of brittle materials. Nature solves this "problem", e.g. in bones, by combining the brittle inorganic (calcium phosphate) phase with fibrous collagen nano-dispersed phase. In present invention, the secondary phases are introduced into the premixed cement phase PBP, such as fibers or secondary particles.

The multi-phase composites are utilized, for example, when there is a need to adjust stiffness of an implant to the stiffness of adjacent bone tissue. This is to avoid the "stress shielding" effect wherein a very stiff implant carries much more stress than less stiff adjacent bone; in the long term, such a "stress-free" bone will tend to resorb, with an increased probability of loosing structural integrity between the implant and the bone (for example, stiff metallic implants are known to cause such effects). In the present invention, the stiffness of the set PBP cement paste can be adjusted by combining the premixed paste with a less stiff organic phase (such as polylactic acid biopolymer, PLA) or low-stiffness porous inorganic phase (such as calcium carbonate or calcium sulphate). The foregoing materials have demonstrated biocompatibility, and resorb so as to provide sufficient space for new bone in-growth and penetration into the set PBP implant volume. In such a capacity, these fillers will not only act to adjust the initial stiffness of the implant, but also will provide macroporosity (1 um-10 mm range) for integration of the non-resorbable set PBP implant with new-grown bone tissue.

Thus, in the present invention, the bio-resorbable secondary phase material or materials are introduced into premixed PBP paste to (i) adjust stiffness of the set composite to the stiffness of adjacent tissue; (ii) resorb and release biological agents such as bisphosphonates for bone growth acceleration or antibiotics to address temporary local infections; and (iii) allow bone in-growth into the space (pores) that are produced during resorption of the secondary phase. The secondary phase particles can be fibers and/or equiaxial (non-fibrous) materials such as PLA or PLGA, calcium carbonate or calcium sulphate. In fibrous form, the secondary phases are primarily intended to increase fracture toughness and tensile strength of the set PBP-based fibrous composite.

Another aspect of the present invention is the use of the PBP cement as injectable scaffold for tissue engineering applications. Currently, scaffolds for bone tissue engineering are pre-fabricated 3D porous matrices with relatively low mechanical strength. The scaffold shape and size has to be designed and processed (machined) according to defect geometry, which can be very complex. This takes a relatively long time, is a costly procedure, and is rather inconvenient for clinical applications. For example, complexly shaped pre-machined scaffolds may be difficult or impossible to insert into bone cavity because of difficult accessibility: This is frequently the case with vertebrae fractures or losses of bone in the skull or jaw.

In the present invention, the PBP (or PBP-based composites) cement is used as an injectable scaffold which in-situ sets and hardens to form high initial strength, 3D matrix scaffold, without the need for pre-design and pre-fabrication processes. This novel concept of PBP-based "injection scaffold" is expected to shorten surgery and patient recovery time, to save scaffolding costs, and to ultimately have better performance as compared to the pre-designed scaffold. Water soluble and biodegradable secondary phases are preferably incorporated into the premixed biocement paste PBP, which dissolve and degrade in human body to provide sufficient porosity of the scaffold. Such as, for example, bioglass, water soluble salts, water soluble metal oxides, calcium phosphates, carbonates and sulphates, biodegradable biopolymers sodium phosphates, magnesium phosphates, bioglass, sodium silicates and mixtures thereof. These phases may also contain medically active ingredients, as may be needed in any particular clinical application. For example, bisphosphonates may be included, so as to be progressively released from the dissolving secondary phase and into adjacent bone tissue to promote new bone ingrowth into the created cavity. The resulting porous biocompatible and bioactive calcium silicate-based scaffold is therefore extremely useful for bone tissue engineering.

Another aspect of the present invention is to include a secondary phase having the effect of removing calcium hydroxide, which is a hydration reaction by-product of calcium silicates. During the setting and hardening of calcium silicate cement, hydration reactions of calcium silicates produce nanosize calcium silicate hydrate gel and calcium hydroxide, resulting in a high pH (pH=10-12) which may damage the adjacent tissue in some applications (although, some dental applications favor high pH if a long-term sterile environment is required, such as in root canal treatment). To address this issue, variants of reactive calcium phosphates of different acidity are included in the PBP composition to react with calcium hydroxide to produce amorphous calcium phosphate (ACP) and/or hydroxyapatite (HAP). This reduces the pH of the cement to around 8-10 (depending on the amount of phosphates added) and increases the mechanical strength and chemical stability of the set PBP cement. The precipitating phosphates, e.g. ACP, HAP or others, are engineered to determine resorbability of the phosphate phase component of the PBP cement in a biological environment. Compounds suitable for reacting with the calcium hydroxide include, but are not limited to, phosphate salts, phosphoric acid, calcium phosphates, sodium phosphates, magnesium phosphates, and organic acids.

Depending on application, the secondary phase in the PBP cement may also comprise metals, metal salts, metal oxides, hydroxide compounds, non-oxide ceramics, biopolymers, and mixtures thereof. The metal salts include, but not limited to, calcium salts, sodium salts, iron salts, magnesium salts, barium salts, strontium salts, potassium salts, zinc salts, phosphates, carbonate, sulfates, silicates, aluminates, hydrogen salts, and a combination and/or a mixture of thereof. The metal oxides include, but not limited to, calcium oxides, sodium oxides, iron oxides, magnesium oxides, barium oxides, strontium oxides, potassium oxides, zinc oxides, zirconium oxide, titanium oxide, tantalum oxides, aluminum oxide, tungsten oxide, bismuth oxide, nickel oxides, cobalt oxides, hafnium oxides, yttrium oxides, silver oxide, gold oxides and a mixture of thereof. The metals include, but are not limited to, stainless steel, irons, titanium, tantalum, aluminum, tungsten, bismuth, nickel, cobalt, hafnium, yttrium, silver, gold, platinum, alloys, and a mixture of thereof. The non-oxides in PBP include, but are not limited to, silicon carbide, silicon nitride, borate silicon, titanium nitride, titanium nitride, nitride-oxide titanium, and a mixture of thereof. The biopolymers include, but are not limited to, biodegradable biopolymers and non-biodegradable polymers. Furthermore, for dental applications, the PBP cement may comprise gutta percha powder for improving sealing abilities and re-treatment abilities.

Additional minor compounds that may be included in the PBP paste compositions of the present invention include, but are not limited to, tricalcium aluminate ($3CaO.Al_2O_3$), tetracalcium aluminoferrite ($4CaO.Al_2O_3.Fe_2O_3$), calcium oxide, ferrite oxide, calcium sulfate dihydrate ($CaSO_4.2H_2O$), sodium salts, magnesium salts, strontium salts, and mixtures thereof, which are less than 30% by weight of cement in the PBP paste composition. Also, the paste may contain a number of impurity oxides from the original raw materials, preferably in a in an amount less than 5% by weight of paste in the cement composition, including, but not limited to, iron oxides, magnesia (MgO), potassium oxide, sodium oxide, sulfur oxides, carbon dioxide, water, and a mixture thereof.

For some dental and orthopedic applications, radio-opaque materials may be added to the PBP paste composition so as to improve absorption of X-rays and thus visibility of the implant in X-ray images. The radio-opaque materials that may be used include, but are not limited to, metals, metal oxides, salts, non-oxides, and mixtures thereof. Examples of such additive materials include Barium sulfate, zirconium oxide, bismuth oxide, tantalum oxide, tantalum, titanium, stainless steel, alloys, and mixtures thereof, which are preferably make up less than about 70% by weight of the PBP paste composition.

Another aspect of the present invention is to use the paste for medical materials and devices, such as prostheses, implants, coatings, and surgical procedures. For example, the premixed PBP pastes are useful for treatment of injuries, fractures and diseases of the musculoskeletal system such as of the spine, joints, ligaments. Conditions treated include bone deformity due to cerebral palsy, osteoarthritis, bone loss due to trauma or disease, scoliosis, implants (hip, knee, shoulder and others), and many others.

As noted above, the injectable PBP cement paste of the present invention does not set and harden in a hermetically sealed package because calcium silicate cements start hydration and harden only when exposed to an aqueous environment. After the paste is placed in contact with a physiological solution, however, diffusional exchange of the non-aqueous carrier with the aqueous solution leads to cement exposure to water, and thus hydration and hardening. These reactions involve hydration of calcium silicate compounds to produce calcium silicate hydrate gel C—S—H and calcium hydroxide CH. The calcium silicate hydrate gel which is biocompatible and bioactive and is the main structural component of cement, contributing to its mechanical strength. As was also noted above, in some embodiments a calcium phosphate compound is added into the PBP paste composition, during setting of the cement, the phosphate ions react with the excess calcium hydroxide resulting from the hydration of the principal components of calcium silicate paste, di-calcium silicate ($2CaO.SiO_2$) and tri-calcium silicates ($3CaO.SiO_2$). In the absence of the phosphate ions, the calcium hydroxide forms inclusions of variable size and shape in the principal gel ($CaO—SiO_2—H_2O$ gel, also expressed as C—S—H) structure. These calcium hydroxide inclusions are weak spots structurally and chemically, i.e. they do not contribute to strength of the set calcium silicate cement and additionally are sensitive to environmental effects. Reacting the CH with phosphate ions, however, produces a variety of calcium phosphate inclusions, the most stable and strongest being hydroxyapatite (HAP). The formation of the C—S—H/HAP composite is accompanied by a decrease of CH content in the set cement, the CH being the weakest component of the set cement structurally and chemically. The resulting material, having a decreased CH content, possesses significantly increased mechanical strength, wherein the calcium phosphate and hydroxyapatite act as a reinforcement phase and calcium silicate hydrate gel is a matrix in the composite structure. Simultaneously, setting pH of the cement decreases, which is advantageous for the majority of medical and dental applications.

The strength of the set PBP cement allows it to be used for both weight and non-weight bearing applications. The PBP cement resists disintegrative washout upon contact with blood, and injection into the wound is less stressful to the surrounding tissue because of it being completely biocompatible with the physiological environment. Therefore, examples of suitable biomedical applications include, but are not limited to, percutaneous vertebroplasty, craniomaxillofacial surgery applications, ridge augmentation, spinal fusion cage/implant, treatment of radial fractures, treatment of temporal mandibular, joint disorders, plastic surgery and cosmetic augmentation, bone graft substitution, veterinary applications, scaffolding, drug delivery, dental applications, apexification, pulp capping, root canal filling and repair, pulpotomy, endodontics, and cominations thereof.

A further aspect of the present invention is a drug eluting capability of PBP-derived implantable medical devices, which combines controlled release of drugs with other functions of prosthetic implants, such as load-bearing functions and scaffold functions. This represents a versatile improvement for implant devices. Orthopedic and dental implants are used to treat bone defects resulting from, for example, disease, trauma, surgical intervention, or congenital deficiencies. Annually, millions of orthopedic implants are placed for fixation and stabilization of fractured bones during healing, or to functionally replace complete tissues (e.g. in total joint replacements). Bone-implant integration (i.e. direct bone-implant bonding) and long-term stabilization is a common clinical problem including infection, bone resorption, implant loosening, slow-healing or non-union. In this aspect of the present invention, bioactive agents are incorporated into the premixed biocement paste PBP for controlled release, for promoting and accelerating bone neogenesis, more reliable bone healing and functional tissue replacement, and preventing infection. The drug-eluting PBP cement functionally improves device performance and the associated quality of life of the patient. Also, multi-bioactive agents can be incorporated into the premixed paste, such as a combination of antibiotic for a short period release (2-3 weeks) to treat the possible short-term infection, and bisphosphonates for long-term release as inhibitors of osteoclastic bone resorption in the treatment of osteoporosis. Bioactive agents that may be incorporated in PBP cement include, but are not limited to, antibiotics, anti-cancer drugs, bisphosphonates, anti-inflammatory drugs, protein drugs, DNA, stem cell, bone growing factors, vitamin drugs, and mixtures thereof.

In another aspect of the present invention, microspheres of PBP biocement paste may be designed for targeted delivery of drugs, proteins, DNA, or other medically active species to an area of interest in the body. The bioactive agents are encapsulated into the microspheres processed out of the PBP paste and are released in a controlled profile once the microspheres are placed in the tissue region of interest and come into contact with body fluids. The release profile of bioactive agents are designed according to the particular clinical requirements, and are controlled by engineering the composition of the PBP paste and the microstructure of the set PBP cement. In one variant, the bioactive agents are encapsulated into biopolymer capsules, liposomes, microphages, emulsions, or core-shell spheres, and then these intermediate carriers are incorporated into the premixed PBP paste for controlled release. Inclusion of such intermediate carriers adds flexibility in pre-designing the multi-drug eluting profiles to match any particular clinical requirements.

In another aspect of the present invention, the flowability and injectability of the PBP paste are improved by controlling the particle size distribution of the solid components in the paste. The particle size of the cement solids is suitably in the range from about 0.01 micrometer to about 1000 micrometers, preferably in the range from about 0.1 micrometer to about 50 micrometers. Also, from organic dispersant agents (coupling agents) may be introduced into the paste to improve the stability and injectability of the paste, including, but not limited to, citric acid, sodium citrate, celluloses, hydroxypropyl methyl cellulose, polyacrylic acids, carbonylmethyl cellulose, biopolymers, organic acids, and mixtures of thereof.

The premixed PBP pastes in accordance with the present invention can be prepared by physical mixing processes (non-reactive), chemical processes (reactive), biological processes, and combinations thereof. For example, a premixed PBP paste can be prepared by mixing the solid phases and water-free liquid using a ball mill process. The coupling agents are deposited on the solid powder surfaces by physical and chemical absorption, improving stability of the premixed paste. The coated solid particles are mixed with the water-free liquid by ultrasound mixer to create uniform paste.

EXAMPLES

Example 1

Preparation of Calcium Silicate Cement PBP Paste

This example illustrates processing of pure PBP calcium silicate paste for biomedical applications. Calcium silicates were fabricated by mixing 151 g calcium oxide and 60 g silica and ball milled in alcohol solution for 24 hours. The mixed powder was dried at 110° C. and fired at 1600° C. for 6 hours. As a result of this process, a homogenous mix of 30 wt % dicalcium silicate and 70% tricalicum silicates powder is obtained, which is further ball milled to achieve average particle size of about 10 micrometers. The premixed biocement paste PBP was made by mixing 100 g of such obtained calcium silicate powder and 21 ml of ethylene glycol in planetary ball mill until full homogenization, which in this example was for a period of 45 minutes. The homogenized calcium silicate PBP paste was filled into a syringe for testing injectability and evaluation of setting characteristics and set cement properties. It was determined that this calcium silicate PBP paste was injectable, of white color, and suitable for dental applications, such as root canal filling, root-end filling material, retrofilling materials, pulp capping, apexification, and the sealing of perforations.

Example 2

Preparation of Phosphate-containing Calcium Silicate PBP Paste

In this example the phosphate silicate paste was prepared synthetically using well defined pure chemicals (as opposed to poorly defined minerals utilized for preparation of typical commercial Portland cement). The raw materials used for the preparation of calcium phosphate silicate powder were colloidal silica (50 wt % Ludox, from 3M company) for $SiO_2$, calcium hydroxide (99.9%, Sigma-Aldrich) for CaO, tetracalcium phosphate ($Ca_4(PO_4)_2O$), and dicalcium phosphate anhydrate ($CaHPO_4.H_2O$) (Fisher). Alternatively, and with no effect on the final properties of paste, the colloidal silica may be derived from thermal decomposition of hydrated silicon alkoxide such as tetra-eth-oxide silicate (TEOS), or added as fine pure silica powder. The designed composition of the cement was 65 wt % tricalcium silicate, 20 wt % dicalcium silicate, 10 wt % tetracalcium phosphate, and 5 wt % dicalcium phosphate. A 200 g batch was prepared by mixing 96.32 g of colloidal silica, 160.98 g of calcium hydroxide, and 300 g distilled water in an alumina jar, and ball milled for 24 hours. The slurry mixture was dried using a spray dryer, and was then fired in a high temperature furnace at 1550° C. for 1 hour to form a mix of tricalcium silicate and dicalcium silicate, and then naturally cooled to room temperature. The resulting cement clinker was ground to −325 sieve particle size (<45 um particle size), with average particle size of about 10 um. 11.25 g of dicalcium phosphate anhydrate was dried in the furnace at 140° C. for 24 hours and then mixed with 20 g of the tetracalcium phosphate and with the fired cement powder (168 grams) in alcohol solution by ball milling for 24 hours. The resulting slurry was spray dried. The average particle size of the cement powder was about 10 um. The paste was prepared by mixing 200 g calcium phosphate silicate powder, 30 g polyethylene glycol (molecular weight 400, Sigma), and 0.5 g hydroxypropyl methyl cellulose, in a planetary ball for 10 minutes. The hydroxypropyl methyl cellulose is a gelling agent for improving the viscosity and flowability of the phosphate-containing PBP paste. The setting time of such prepared PBP paste at 37° C. in 100% humidity environment was about 10 hours. The average compressive strength after 7-day setting at 37° C. and 100% humidity was 101 MPa, with the standard deviation of 8 MPa. This PBP cement paste was injectable and suitable for dental and orthopedic applications.

Example 3

In Vitro Testing of Bioactivity of the PBP Paste Cements

This example illustrates bioactivity of calcium phosphate silicate PBP paste. The paste was prepared by the process described above in Example 2. The cement paste was filled into a cylinder mold having a 1 inch diameter and 2 inch height. The samples were incubated at 100% humidity without use of any organic species, and pH was adjusted to 7.4 with 7.5% $NaHCO_3$ solution. All samples were immersed in SBF solution at 37° C. for 10 days, and then the samples were washed with distilled water and dried for SEM observations. It was found that a typical hydroxyapatite structure layer had formed on the surface of the cement, as shown in FIG. 1. These results demonstrate that the PBP cement of the present invention has good bioactivity, osteoinductivity, and osteogenicity.

Example 4

PBP Paste Composition with Radio-Opaque Component for Dental Applications

This example illustrates a procedure for making calcium silicate PBP dental paste incorporating radio-opaque material. The fired cement powders were prepared as described above in Example 2. Zirconia ($ZrO_2$, Zircoa, USA) was chosen as the radio-opaque material for dental application because zirconia is biocompatible and used for orthopedic implant devices. Alternatively, and with no effect on the final properties of the paste, the radio-opaque material may be derived from tantalum oxide $TaO_2$. The paste was prepared by mixing 70 g of the cement powder, 30 g of zirconia, and 10 g ethylene glycol in a ball mill for 20 minutes. X-ray tests indicated clear visibility of the modified paste, demonstrating that the dental cement with zirconia radio-opaque is suitable for dental applications. The radio opacity of paste was characterized according to the ISO standard, ANSI/ADA No. 57:2000 Endodontic Sealing Materials, ISO 3665 Photography—Intra-oral dental radiographic film—Specification, and ISO 6876:2001 Dental root canal sealing materials. The radio-opacity of the cement was more than that of 4 mm thick aluminum wedge.

Example 5

PBP Paste Composition for Dental Applications

The following procedure illustrates preparation of a high strength, pure, bioactive, and biocompatible PBP paste for dental applications. Raw materials used for the example were colloidal silica (50 wt % Ludox, 3M) for $SiO_2$, calcium hydroxide (99.9%, Sigma-Aldrich) for CaO, boehmite (AlOOH) for $Al_2O_3$, iron oxide ($Fe_2O_3$, 99% Fisher), calcium sulfate dehydrate ($CaSO_4.H_2O$, 99%, Fisher), $Ca(OH)_2$, and monocalcium phosphate ($Ca(H_2PO_4)_2$, 99%, sigma). Alternatively, and with no effect on the final properties of the paste, the colloidal silica may be derived from thermal decomposition of a hydrated silicon alkoxide such as tetra-eth-oxide silicate (TEOS). The designed composition of the present cement was 58 wt % tricalcium silicate ($3CaO.SiO_2$), 11 wt % dicalcium silicate ($2CaO\ SiO_2$), 6 wt % tricalcium aluminate ($3CaO.Al_2O_3$), 7 wt % tetracalcium aluminoferrite ($4CaO.Al_2O_3.Fe_2O_3$), 4 wt % calcium sulfate dehydrate ($CaSO_4.2H_2O$), 4 wt % calcium oxide, and 10 wt % monocalcium phosphate ($Ca(H_2PO_4)_2$). A 200 g batch was prepared by mixing 78 g colloidal silica, 156.9 g calcium hydroxide, 10.57 g boehmite, 4.61 g ferrite oxide, and 300 g distilled water in an alumina jar and ball milled for 24 hours. The slurry mixture was dried by using a spray dryer, and was then fired in a high temperature furnace at 1550° C. for 1 hour, and then naturally cooled to room temperature, followed by grinding to about 10 um average particle size. 20 g of monocalcium phosphate, 8 g of calcium hydroxide, and 8 g of calcium sulfate dehydrate were mixed with the fired cement powder and 35 g polyethylene glycol 600 by planetary ball mill for 5 minutes. The paste was filled into a syringe for evaluation. This cement PBP paste was injectable, of gray color, and suitable for dental applications, such as root-end filling material, retrofilling materials, pulp capping, apexification, and the sealing of perforations. For making white color PBP cement for the specific dental applications requiring color control (e.g. for cosmetic reasons), all the process of cement preparation was repeated exactly, except that the iron oxide was excluded from the cement composition. The properties of such white variant of PBP were essentially the same as the properties of the gray variant of the PBP as illustrated in FIGS. 3, 4A, and 5A-B.

Example 6

PBP Paste Composition for Drug Delivery Applications

This example illustrates incorporation of bioactive agents into the PBP paste for subsequent controlled release into a biological environment. The paste was prepared as described in Example 1, additionally containing the antibiotic agent vancomycin in the amount of 1 wt % and 5 wt %, respectively.

Figure 2:
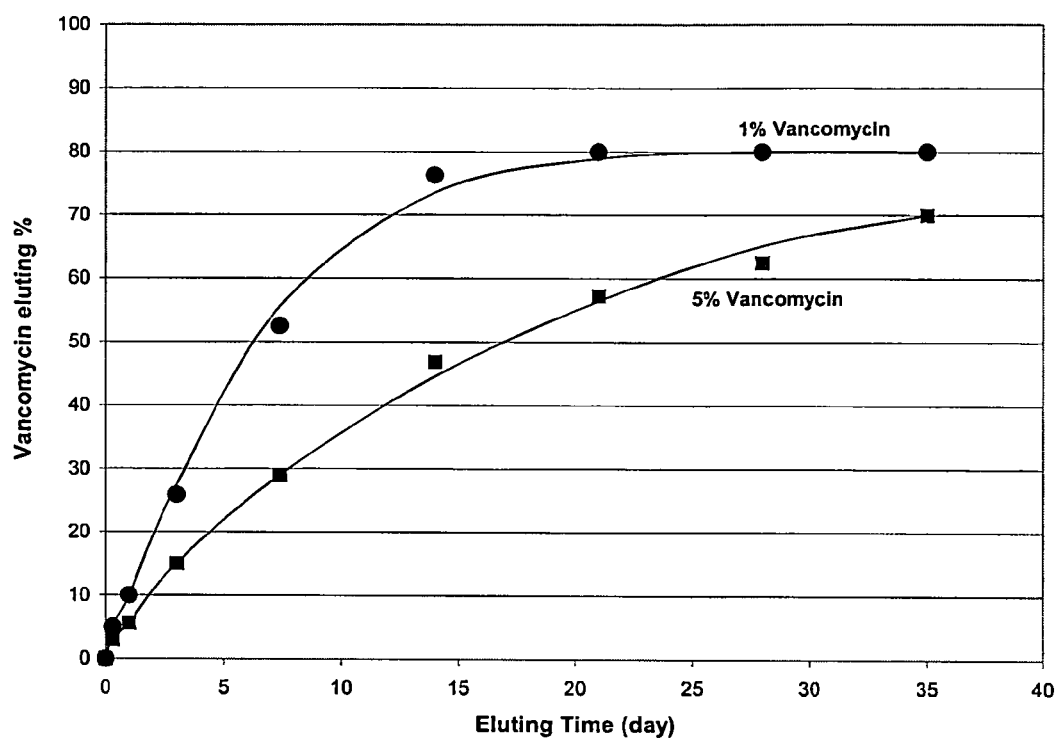
FIG. 2 is a graph illustrating the eluting profiles of Vancomycin (an antibiotic) in-vitro, from PBP cement pastes in accordance with the present invention, containing 1 wt % and 5 wt % Vancomycin.

The PBP paste was injected into the bone void and then placed into water-based phosphate buffer solution, such that hardening initiated immediately through exchange of PEG into water in the paste. Simultaneously, the antibiotic drug was released from the paste into PBS solution. PBP Cement paste #2 contained 5 wt % of Vancomycin and proportionally less other components. It is observed that vancomycin releases within 2 weeks from PBP paste #1 (containing 1% vancomycin), and within 5 weeks from PBP paste #2 containing a higher content (5% vancomycin). In both cases, the released concentrations were higher than the concentration effective against different types of *Staphylococcus aureus* resistant to Meticilin-Cefem (MRSA). The rate of drug release depended on the composition of the paste, but for the two periods studied up to 80% of the antibiotic was liberated in both cases, as illustrated in FIG. 2.

Example 7

Biological Evaluation of Premixed Silicate PBP Paste

This example demonstrates the biological properties of premixed PBP paste for medical applications. The samples were prepared as described in Example 2. The Sensitization study was chosen because it would determine whether the PBP cement of the present invention contained chemicals that might interact with body's immune system in a manner that could cause adverse local or systemic effects after repeated or prolonged exposure. Because such sensitization (allergic) or hypersensitivity reactions to biomaterials have been of the dermal cell-mediated, rather than humoral or antigen-antibody type, the skin of laboratory animals was used in the sensitivity tests. Dermal sensitization reactions in laboratory animals are marked by redness and swelling. Guinea pigs were used because they are a species known to be nearly as responsive to dermal sensitizers as human beings. The Guinea Pig Maximization Test (Magnusson-Kligman Method) is the most sensitive test method for delayed hypersensitivity and is recommended for testing devices, chemicals and materials that have externally communicating or internal contact with the body or body fluids. In this study, the test material is mixed with complete Freund's adjuvant (CFA) to enhance the skin sensitization response. This test is considered more sensitive than the repeated-patch model; the Maximization Test is used for device materials that will contact areas other than skin. The test results show that the premixed cement PBP paste of the present invention did not produce any significant dermal reaction. The results for the injection phase, induction phase and the challenge phase showed no erythema and no oedema after 24 hours. The weight of treated animals during each of these phases exhibited a satisfactory weight gain compared with the weight of the control animals. The premixed cement paste of the present invention produced no delayed contact dermatitis (Type IV sensitization), and furthermore did not produce an allergic potential after multiple uses. A negative result in such a sensitive assay ensures a considerable safety margin regarding the potential risk to humans.

The Genotoxicity study was chosen because it provided an in vitro method to detect mutagens, substances that can directly or indirectly induce genetic damage directly through a variety of mechanisms. The Microbial Reverse Mutation Assay or Ames test detects point mutations by employing several strains of the bacteria *Salmonella typhimurium*, which have been selected for their sensitivity to mutagens and various DNA active substances. Potential mutagencity was evaluated in the presence and absence of a mammalian liver S-9 activation system. Mammalian liver S-9 activation system accounts for enzyme activation or pro-mutagens or deactivation of direct acting mutagens. The test results indicated that the premixed cement PBP did not induce mutagenic activity by a Microbial Reverse Mutation Assay (Ames Assay) with or without S-9 enzyme activation. The positive controls in the test produced anticipated mutagenic responses, thus validating the test results for the premixed cement of the present invention.

The Implantation study was chosen because it assessed the local pathological tissue effects and response around surgically implanted cement in accordance with the present invention in contact with living tissue, at both the gross level and microscopic level. The histopathology analysis assesses the dynamics of the biochemical exchange and cellular and immunologic responses of the tissues in the implantation study. The implantation technique evaluates both absorbable and non-absorbable materials. For a material, this test is equivalent to subchronic toxicity tests for materials.

Because the present premixed PBP cement is designed to be used inside the human body for a long period of time, implanting samples inside the body of a laboratory animal is the most direct means of evaluating medical device materials potential effects on the surrounding living tissue. Consequently, the premixed PBP cement of the present invention was surgically implanted in the subcutaneous skin of rabbits, the rabbit has become the species of choice for implant studies because of their susceptibility to systemic dermal toxic action of most substances and the easy accessibility for performing implants. Implantation in the subcutaneous tissue of rabbits was performed during two periods: 15 days and 3 months. For each period, three rabbits were implanted each with the premixed cement. Throughout the study the rabbits gained a good weight, especially in the rabbits involved in the 3 month study. Macroscopic and microscopic histology analysis concluded that the premixed cement of the present invention was tolerated well by the subcutaneous tissue.

Example 8

Application of Premixed Silicate PBP Paste as Dental Root Canal Sealer

Figure 3:
FIG. 3 is an X-ray micro-photograph of two teeth with fillings formed using cement in accordance with the present invention, showing fillings made without and with gutta percha points.
Figure 4A:
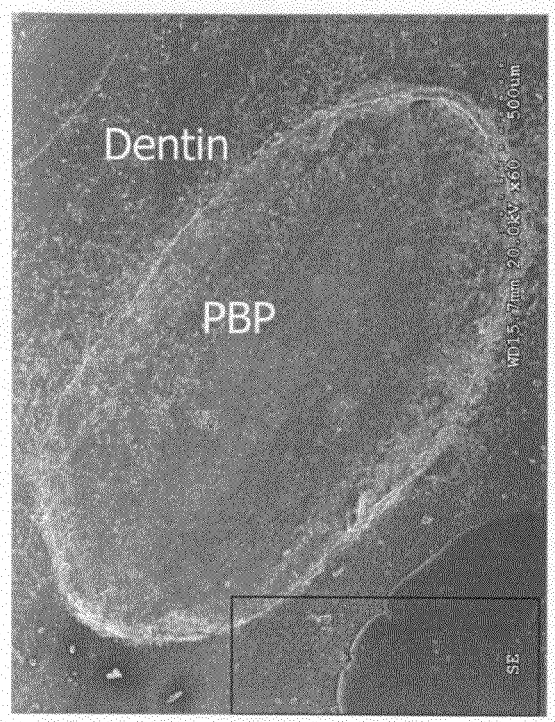
FIG. 4A is a medium-scale magnification of a cross-section through the tooth of FIG. 3 in which the filling is formed without gutta percha points, showing the complete filling and absence of gaps achieved using the cement of the present invention.
Figure 4B:
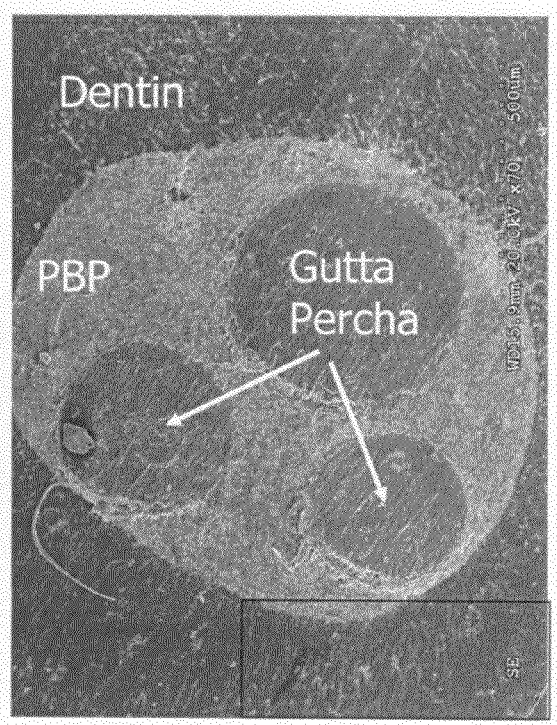
FIG. 4B is a medium-scale magnification of a cross-section through the tooth of FIG. 3 in which the filling includes gutta percha points, again showing complete filling by the cement of the present invention.
Figures 5A, 5B:
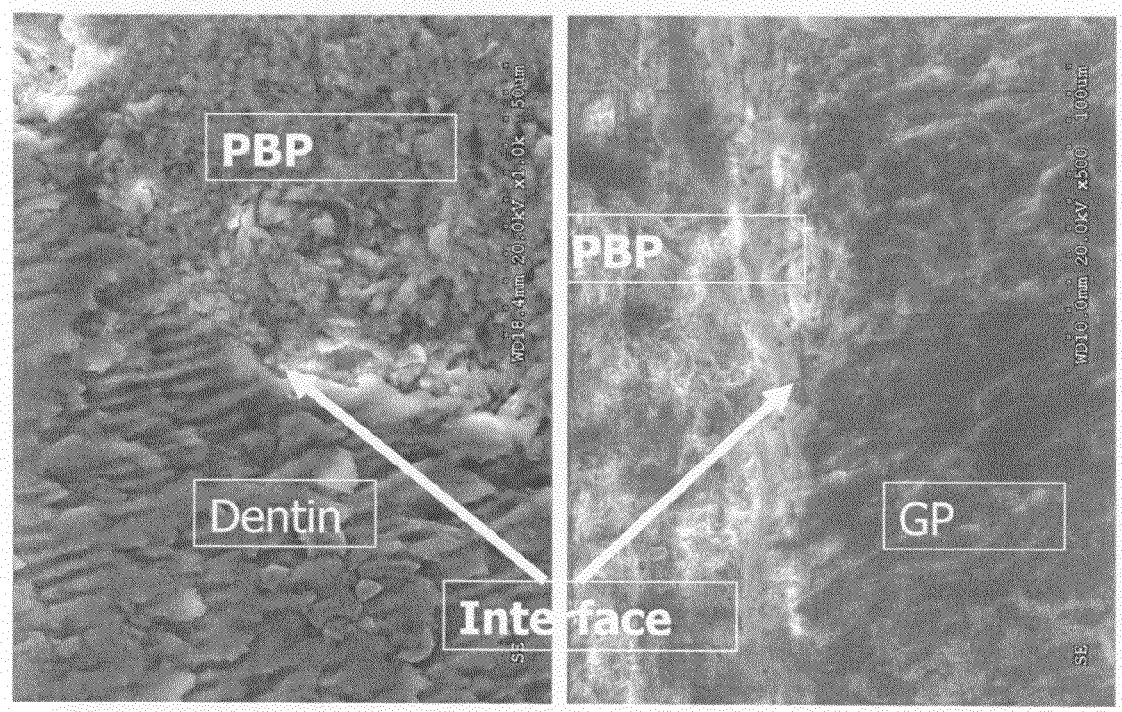
FIG. 5A is a high-scale magnification of the cross-section of FIG. 4A, showing in greater detail the interface between the cement filling and the dentin of the tooth.
FIG. 5B is a high-scale magnification of the cross-section of FIG. 4B, showing in greater detail the interface between the cement filler and all of the gutta percha points.

This example demonstrates applicability of the premixed PBP paste for effectively sealing root scanal during endodontic treatment. The PBP paste was prepared as described in Example 4. Extracted teeth were used for performing the root canal filling with the PBP cement and gutta percha. The setting time of the PBP cement in the root canal is dependent upon the availability of moisture for the hydration reaction of the calcium silicates in the paste. The teeth were filled using the PBP paste and taper 0.02 ISO standard Gutta Percha Points. A lateral condensation technique was used for the root canal filling. The tip of a syringe containing the PBP paste was inserted into the deepest part of the root canal. The PBP paste was dispensed gently and smoothly into the apex of the root canal by compressing the syringe piston. The syringe was withdrawn gradually while the PBP paste was compressed into the canal. Subsequently, the root canal was filled in a conventional manner using the gutta percha points. After filling, extra (overflow) PBP paste was removed with moist cotton pellets and the root canal coronal foramen was sealed with nail varnish twice. In order to compare different delivery systems, the PBP paste was also used to fill the canals without gutta percha points. The filled teeth were plaaced into 100% humidity 37° C. incubator for 7 days. After 7 days setting, radiographs were taken of the teeth randomly to assess quality of the filling with the PBP cement with/without gutta percha (GP). The results are illustrated in FIG. 3: Careful examination of the X-ray radiograms indicates nearly perfect filling of the canal volume with PBP cement, both with and without GP. However, in order to assess the seal quality at microscale level, scanning electron microscopy (SEM) examination needs to be performed on cross-sections through the teeth; to also, to assess progress of hydration and setting, cross-sections have to be evaluated with a Vicat probe. Therefore, using a diamond saw, the teeth were therefore cut to open the cross-section in the coronal one third, middle one third and apical one third separately. The apical one-third cross-section was observed under SEM and the results are shown in FIGS. 4A-4B (medium magnification; size bar=500 µm), and 5A-B (high magnification; size bar=50 µm). No gaps are visible at any of the interfaces (i.e. the dentin/PBP and GP/PBP interfaces), both at medium and high magnification. The SEM results therefore indicate that the PBP cement forms an intimate bond both with dentin and Gutta Percha Points. The high-magnification SEM, which is shown in FIG. 5A, also illustrates that the PBP cement diffused into the tubules of dentin: Such an interlocked, intimate interface between the cement and dentin provides an excellent seal of the root canal, effectively preventing bacteria leakages. In addition to the SEM observations, the coronal one third of the sealed root was probed for setting time with a Vicat needle, according to standard test method of dental water-based cements (ISO9917:1991). The setting time was determined to be 10 hrs.

What is claimed is:

1. A premixed hydraulic cement paste for use in medical or dental applications, said cement paste comprising:
   at least one calcium silicate compound, in an amount in the range from about 20% to about 95% by weight percent of said paste; and
   at least one substantially water-free liquid carrier mixed with said at least one calcium silicate compound, that undergoes exchange with an aqueous physiological solution so that water in said aqueous physiological solution contacts and reacts with said at least one calcium silicate compound to produce hydraulic gel and calcium hydroxide, so that said cement paste hydrates and hardens when placed in a physiological environment.

2. The premixed hydraulic cement paste of claim 1, wherein said at least one calcium silicate compound is selected from the group consisting of:
   calcium silicate;
   dicalcium silicate;
   tricalcium silicate; and
   mixtures thereof.

3. The premixed hydraulic cement paste of claim 1, wherein said substantially water-free liquid carrier is selected from the group consisting of:
   ethylene glycol;
   polyethylene glycol;
   liquid glycerol;
   glycerin;
   ethyl alcohol;
   vegetable oil;
   animal oil;
   silicon oil;
   hydroxylpropyl methycellulose; and
   mixtures thereof.

4. The premixed hydraulic cement paste of claim 1, wherein said substantially water-free carrier liquid comprises:
   no more than about 20% water by weight percent of said paste.

5. The premixed hydraulic cement paste of claim 1, comprising said at least one calcium silicate compound in an amount in the range from about 30% to about 70% by weight percent of said paste.

6. The premixed hydraulic cement paste of claim 1, comprising said substantially water-free liquid carrier in an amount in the range from about 5% to about 70% by weight percent of said paste.

7. The premixed hydraulic cement paste of claim 6, comprising said substantially water-free liquid carrier in an amount in the range from about 10% to about 40% by weight percent of said paste.

8. The premixed hydraulic cement paste of claim 1, further comprising:
   at least one secondary phase for enhanced performance when said paste is set in said physiological environment.

9. The premixed hydraulic cement past of claim 8, wherein said secondary phase comprises:
   at least one radio-opaque material for enhanced x-ray imaging of said set cement paste.

10. The premixed hydraulic cement paste of claim 9, comprising
    said radio-opaque material in an amount less than about 70% by weight percent of said paste.

11. A premixed hydraulic cement paste for use in medical or dental applications, said cement paste comprising:
    at least one calcium silicate compound in an amount in the range from about 30% to about 70% by weight percent of said paste, said at least one calcium silicate compound being selected from the group consisting of:
    calcium silicate;
    dicalcium silicate;
    tricalcium silicate; and
    mixtures thereof; and
    at least one substantially water-free liquid carrier mixed with said at least one calcium silicate compound, that undergoes exchange with an aqueous physiological solution so that water in said aqueous physiological solution contacts and reacts with said at least one calcium silicate compound to produce hydraulic gel and calcium hydroxide, so that said cement paste hydrates and hardens when placed in a physiological environment, in an amount in the range from about 30% to about 70% by weight percent of said paste, said substantially water-free liquid carrier being selected from the group consisting of:
    ethylene glycol;
    polyethylene glycol;
    ethyl alcohol;
    vegetable oil;
    animal oil;
    silicon oil;
    hydroxypropyl methylcellulose; and
    mixtures thereof.

12. A premixed hydraulic ceramic cement paste for use in medical or dental applications, said cement paste consisting of:
    at least one calcium silicate compound; and
    at least one substantially water-free liquid carrier mixed with said at least one calcium silicate compound, that undergoes exchange with an aqueous physiological solution so that water in said aqueous physiological solution contacts and reacts with said at least one calcium silicate compound to produce hydraulic gel and calcium hydroxide, so that said cement paste hydrates and hardens when placed in a physiological environment.

13. The premixed hydraulic ceramic cement paste of claim 12, wherein said at least one calcium silicate compound is selected from the group consisting of:
- calcium silicate;
- dicalcium silicate;
- tricalcium silicate; and
- mixtures thereof.

14. The premixed hydraulic ceramic cement paste of claim 12, wherein said substantially water-free liquid carrier is selected from the group consisting of:
- ethylene glycol;
- polyethylene glycol;
- liquid glycerol;
- glycerin;
- ethyl alcohol;
- vegetable oil;
- animal oil;
- silicon oil;
- hydroxylpropyl methycellulose; and
- mixtures thereof.

* * * * *